United States Patent [19]

Piwinski et al.

[11] Patent Number: 4,804,666
[45] Date of Patent: Feb. 14, 1989

[54] ANTIALLERGIC 6,11-DIHYDRO-11-(4-PIPERIDYLIDENE)-5H-BENZO(5,6)CYCLOHEPTA(1,2-B)PYRIDINES

[75] Inventors: John J. Piwinski, Parsippany; Michael J. Green, Skillman; Ashit K. Ganguly, Upper Montclair; Jesse K. Wong, Union; Bernard Katchen, Livingston; Jeffrey Cramer, Westfield, all of N.J.

[73] Assignee: Schering Corporation, Kenilworth, N.J.

[21] Appl. No.: 43,409

[22] Filed: Apr. 28, 1987

Related U.S. Application Data

[63] Continuation-in-part of Ser. No. 765,613, Aug. 14, 1985, abandoned.

[51] Int. Cl.[4] .................. A61K 31/445; C07D 401/08
[52] U.S. Cl. .................................... 514/278; 514/290; 546/15; 546/93
[58] Field of Search .................. 546/15, 93; 514/290, 514/278

[56] References Cited

U.S. PATENT DOCUMENTS

| 3,326,924 | 6/1967 | Villani | 546/93 |
| 4,273,780 | 6/1981 | Waldvogel et al. | 546/202 X |
| 4,282,233 | 8/1981 | Villani | 546/93 X |
| 4,355,036 | 10/1982 | Villani | 546/93 X |

Primary Examiner—Richard A. Schwartz
Attorney, Agent, or Firm—James R. Nelson; Stephen I. Miller; Richard C. Billups

[57] ABSTRACT

Derivatives of 6,11-dihydro-11-(4-piperidylidene)-5H-benzo[5,6]cyclohepta[1,2-b]pyridine, and pharmaceutically acceptable salts and solvates thereof are disclosed, which possess anti-allergic activity, making them effective as anti-allergic compounds. Methods for preparing and using the compounds are also described.

24 Claims, No Drawings

ANTIALLERGIC 6,11-DIHYDRO-11-(4-PIPERIDYLIDENE)-5H-BENZO(5,6)CYCLOHEPTA(1,2-B)PYRIDINES

CROSS REFERENCE TO RELATED APPLICATIONS

This is a Continuation-in-Part of U.S. Application Ser. No. 765,613 filed August 14, 1985, now abandoned, priority of which is claimed hereunder.

BACKGROUND OF THE INVENTION

The present invention relates to certain 6,11-dihydro-11-(4-piperidylidene)-5H-benzo [5,6]cyclohepta [1,2-b]pyridines and to pharmaceutical compositions and methods of using such compounds.

U.S. Pat. Nos. 3,326,924, 3,717,647 and 4,282,233, European published application No. 0042544 and Villani et al., Journal of Medicinal Chemistry, Vol. 15, No. 7, pp 750-754 (1972) and Villani et al. Arzneim-Forsch Drug Res., Vol. 36, p. 1311 (1986) describe certain 11-(4-piperidylidene)-5H-benzo[5,6]cyclohepta[1,2-b]pyridines as antihistamines. U.S. Pat. No. 4,355,036 describes certain N-substituted piperidylidene compounds.

SUMMARY OF THE INVENTION

This invention is a compound having the structural formula I:

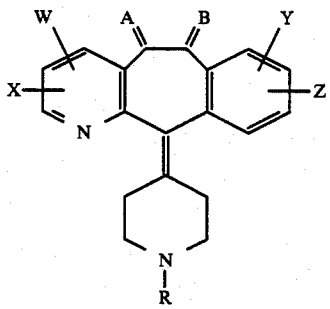

or a pharmaceutically acceptable salt or solvate thereof, wherein:

R represents H or alkyl, such that
(1) when R represents alkyl,
at least one of A and B represents a substituent group selected from H and $OR^1$, H and $OC(O)R^1$, $=NOR^1$ or $-O-(CH_2)_n-O-$, and the other may represent $H_2$ or one of the above listed substituent groups;
W, X, Y and Z may be the same or different and each independently represents H, halo, alkyl, $-CF_3$, $-NO_2$, $-OC(O)R^1$, $-SR^1$, $-OR^1$, $-CO_2R^1$ or $-N(R^1)_2$;
$R^1$ is H, alkyl or aryl and in $N(R^1)_2$, $R^1$ can be alkanediyl, and n is 2, 3 or 4, and
(2) when R represents H,
A or B may be the same or different and each independently represents $H_2$, H and $OR^1$, H and $OC(O)R^1$, $=O$, $=NOR^1$ or $-O-(CH_2)_n-O-$;
W, X, Y and Z may be the same or different and each independently represents H, halo, alkyl, $-CF_3$, $-NO_2$, $-OC(O)R^1$, $-SR^1$, $-OR^1$, $-CO_2R^1$ or $-N(R^1)_2$, with the provisos that when A and B both represent $H_2$, W is OH, and when A and B represents $=O$, at least one of W, X, Y and Z represents halo, alkyl, $-CF_3$, $-NO_2$, $-OC(O)R^1$, $-SR^1$, $-OR^1$, $-CO_2R^1$ or $-N(R^1)_2$, and
$R^1$ and n are as defined above.

The invention further encompasses a compound as defined above, wherein R represents alkyl; at least one of A and B represents a substituent group selected from H and $OR^1$, H and $OC(O)R^1$, $=NOR^1$ or $-O-(CH_2)_n-O-$, and the other may represent $H_2$ or one of the above listed substituent groups; W, X, Y and Z may be the same or different and each independently represents H, halo, alkyl, $-CF_3$, $-NO_2$, $-OC(O)R^1$, $-SR^1$, $-CO_2R^1$ or $-N(R^1)_2$, wherein $R^1$ is H, alkyl or aryl, and n is 2, 3 or 4.

The invention is further described as encompassing a compound of formula I wherein R is for example, lower alkyl.

The invention further encompasses a compound of formula I wherein R is lower alkyl of from 1 to 3 carbon atoms.

The invention described herein further encompasses a compound as described above, wherein R represents H; A or B may be the same or different and each independently represents $H_2$, H and $OR^1$, H and $OC(O)R^1$, $=O$, $=NOR^1$ or $-O-(CH_2)_n-O-$; W, X, Y and Z may be the same or different and each independently represents H, halo, alkyl, $-CF_3$, $-NO_2$, $-OC(O)R^1$, $-SR^1$, $-OR^1$, $-CO_2R^1$ or $-N(R^1)_2$, with the provisos that when A and B both represent $H_2$, W is $-OH$, and when A or B represents $=O$, at least one of W, X, Y and Z represents halo, alkyl, $-CF_3$, $-NO_2$, $-OC(O)R^1$, $-SR^1$, $-OR^1$, $-CO_2R^1$ or $-N(R^1)_2$, with $R^1$ and n as previously defined.

The invention described herein further encompasses a compound having R equal to H, one of A and B equal to $H_2$ and the other equal to H and $OR^1$, H and $OC(O)R^1$, $=O$, $=NOR^1$ or $-O-(CH_2)_n-0-$, with W, X, Y, Z, $R^1$ and n as previously defined.

The invention described herein further encompasses a compound having R equal to H and wherein at least one of A and B represents H and $OR^1$.

The invention described herein further encompasses a compound having R equal to H, A and B each representing $H_2$ and W representing $OR^1$, with $R^1$ as previously defined, for example, with $R^1$ equal to H.

The invention described herein further encompasses a compound of formula I wherein R equals H and one of Y and Z represents halo, for example, where Y represents halo (e.g., chloro), at position 8.

The invention described herein further encompasses a compound of formula I having R equal to H, wherein at least one of W and X represents $-OR^1$, for example, where W represents $OR^1$ attached to position 3, and $R^1$ represents H.

The invention described herein further encompasses the compounds of formula I wherein R is H or alkyl, and W, X, Y and Z independently represent H, halo, alkyl, $-CF_3$, $-SR^1$, $-OR^1$ or $-N(R^1)_2$, for example, where at least one of Y and Z is halo.

The invention described herein further encompasses the compounds of formula I wherein R is H or alkyl and one of W and X is $OR^1$, with $R^1$ as previously defined.

In a preferred embodiment of the invention, R represents $-H$ or lower alkyl. More preferably, R represents alkyl having from 1-3 carbon atoms.

The preferred embodiments of the invention further include those where A or B represent $-OH$, $=O$, OH or $=N-OR^1$, wherein $R^1$ is as previously defined.

Preferred W, X, Y, and Z groups include —H, —OH, and halo, and the most preferred values for W, X, and Y are —H. The most preferred value for Z is halo, and in particular —Cl.

Preferred compounds of the invention include:

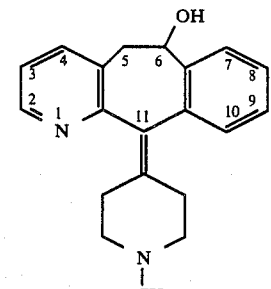

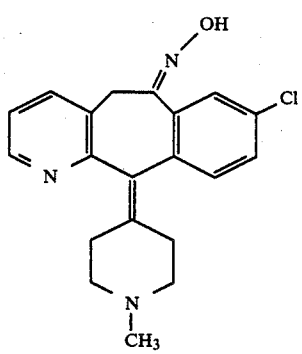

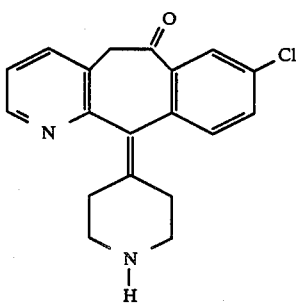

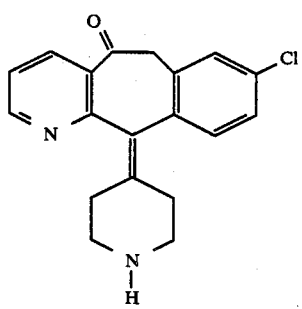

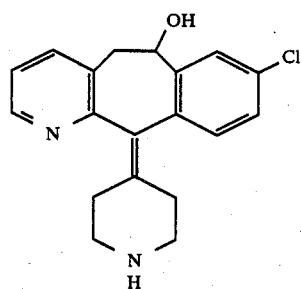

-continued

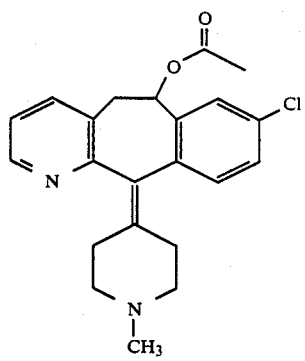

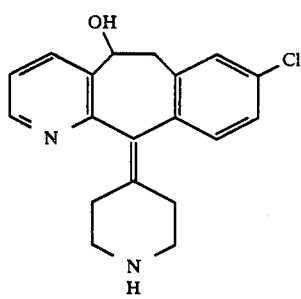

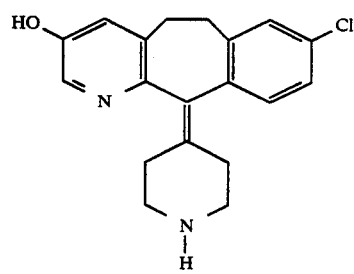

The invention includes a composition which comprises a compound of formula I as defined above in combination with a pharmaceutically acceptable carrier.

The invention further includes a method of treating allergy in a mammal which comprises administering the above defined compound of formula I to said mammal in an amount effective to treat allergy.

As used herein, the following terms are used as defined below unless otherwise indicated:

alkyl—(including the alkyl portion of substituted alkyl, the divalent alkyl moiety of alkanediyl and dialkylamino) straight, branched or cyclic carbon chains containing from 1 to 20 carbons;

lower alkyl—straight or branched carbon chain of from 1 to 6 carbon atoms;

aryl—(including the aryl portion of substituted aryl, arylthio and aryloxy) represents a carbocyclic group containing from 6 to 15 carbon atoms and having at least one aromatic ring (e.g., aryl is a phenyl ring), with all available substitutable carbon atoms of the carbocyclic group being intended as possible points of attachment; and halo—represents fluoro, chloro, bromo and iodo.

DESCRIPTION OF THE INVENTION

Certain compounds of the invention may exist in isomeric forms. The invention contemplates all such isomers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As noted above, the pyridine and benzene ring structures of formula I may contain one or more substituents W, X, Y and Z. In compounds where there is more than one such substituent, they may be the same or different. Thus compounds having combinations of such substituents are within the scope of the invention. Also, the lines drawn into the rings from the W, X, Y and Z groups indicate that such groups may be attached at any of the available positions. For example, the W and X groups may be attached at the 2, 3 or 4 positions while the Y and Z groups may be attached at any of the 7, 8, 9 or 10 positions.

Carbon atoms 5 and 6 of formula I are referred to as the "bridgehead carbons", and may each contain one or more substituents. Carbon atom 5 may be substituted with group A and carbon atom 6 may be substituted with group B. Where more than one group is attached, they may be the same or different.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts for example, the piperidino or pyridino nitrogen can form salts with strong acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention and all acid and base salts are considered equivalent to the free forms of the corresponding compounds for purposes of the invention.

The following process may be employed to produce compounds of structural formula I. For the compounds II through XIII which are substituted at one bridgehead carbon atom, the substitution group shown may have a bond drawn into the cycloheptane ring through the bridgehead, rather than to a specific bridgehead carbon atom. This is used to indicate that attachment of the substitution group to a particular bridgehead carbon atom is a function of the starting compound. For example, if the methoxy group of compound II below is attached to bridgehead carbon 5, the carbonyl group on the bridgehead of compound III will be positioned at carbon 5 also. However, both isomers are contemplated as being within the scope of the invention.

By substituting an isomer of the precursor compound, a compound can be synthesized having the substitution on the bridgehead carbon atoms different from that disclosed in the drawing.

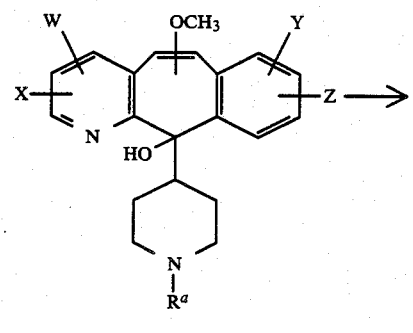

II

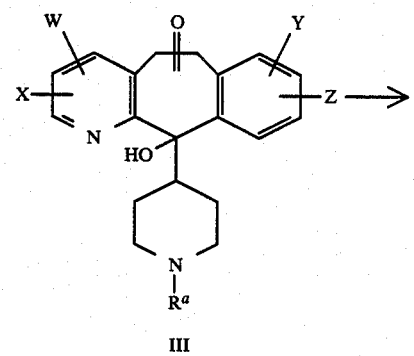

III

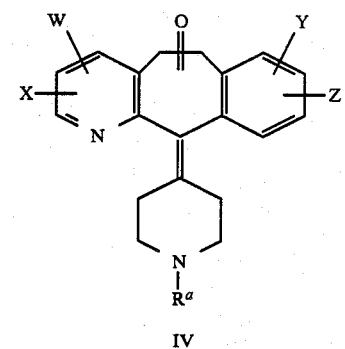

IV

A compound of formula II wherein $R^a$ is alkyl may be hydrolyzed with any strong, aqueous acid, for example, 80–95% $H_2SO_4$ or HCl, having a pH less than 1, at a temperature no higher than room temperature for not generally longer than one hour to produce an intermediate compound of formula III.

After complete hydrolysis, compound III may be dehydrated with $CF_3SO_3H$ (triflic acid) or a similar acid to yield compound IV which is a compound of the invention, falling within the scope of compound I. Examples of other acids for dehydrating compound III at carbon atom 11 include, for example, $HF/BF_3$, $CH_3SO_3H/BF_3$, etc. The reaction can be performed in the absence of or with an inert co-solvent such as $CH_2Cl_2$. The temperature and time of the reaction vary with the acid employed. When triflic acid is used as the super acid system, the temperature may be controlled to minimize side reactions. For example, Compound III having a carbonyl at carbon atom 5 is best dehydrated when the temperature is maintained in the range of from about 40° C. to about 80° C., preferably about 75° C. Alternatively, dehydration of a compound having a carbonyl at carbon atom 6 is best accomplished at elevated temperatures, such as from about 100° C. to 130° C.

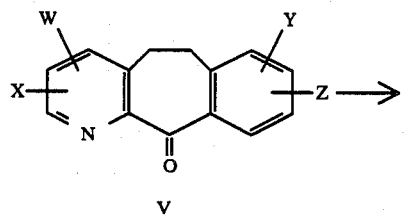

V

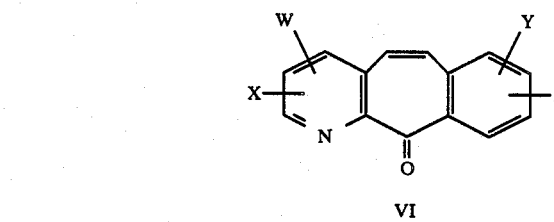

VI

The alkoxy compound of formula II may be prepared from a starting material of formula V, which is disclosed in U.S. Pat. No. 3,326,924. The bridgehead of Compound V is first brominated with an appropriate brominating agent, such as N-bromosuccinimide (NBS) in the presence of an initiator, such as azobisisobutyryl nitrile (ABIN), benzoyl peroxide or the like in an inert solvent, such as CCl₄, benzene or a similar solvent. Heat or light may be required to initiate the reaction. The bromine on the bridgehead may then be eliminated with base to form the olefinic Compound VI. Examples of suitable bases for elimination include diazabicycloundecane (DBU), diazabicyclononane (DBN) and diazabicyclooctane (DABCO). Elimination is typically performed in an inert solvent at reflux temperature. Examples of suitable inert solvents include CH₂Cl₂, CCl₄, toluene, tetrahydrofuran (THF), dioxane, and CHCl₃, with CHCl₃ being preferred.

Alternatively, Compound V may be refluxed in the presence of an oxidizing agent to yield compound VI. Representative examples of oxidizing agents suitable for oxidizing compound V include 2,3-dichloro-5,6-dicyano-1,4-quinone (DDQ) and SeO₂.

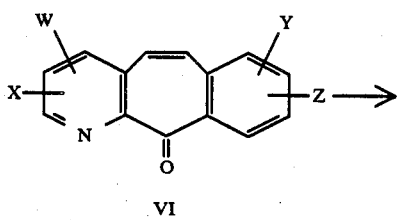

VI

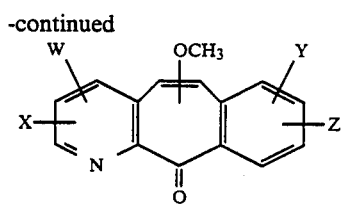

VII simple aqueous hydrolysis

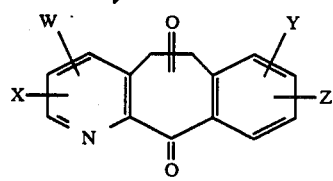

Compound VI may be converted to Compound VII by adding excess powdered AgNO₃ in methanol, followed by the addition of excess Br₂, which bromoetherificates the unsubstituted bridgehead carbon atom. The bridgehead bromine is then eliminated with excess base, such as DBU to provide a compound of formula VII. The reaction may be run in an inert solvent such as CHCl₃ at reflux temperature. The resultant isomeric mixture may be separated by column chromatography or any other appropriate method.

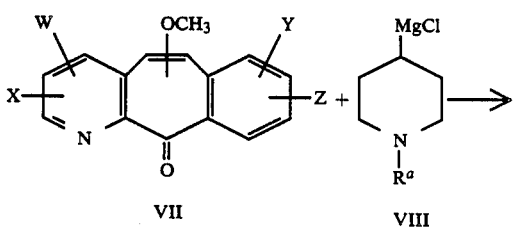

VII         VIII

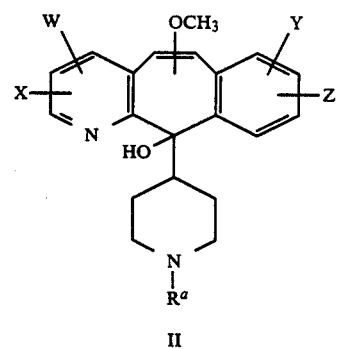

II

A compound of formula II is prepared by treating the 5-substituted or 6-substituted isomer represented by compound VII with a Grignard reagent VIII in an inert solvent, such as ether, benzene, or tetrahydrofuran (THF). Compound VIII where $R^a$ equals alkyl is prepared in a known manner from magnesium and the 4-chloro N-substituted piperidine. The reaction may be refluxed if necessary, after which it may be quenched with NH₄Cl to form compound II.

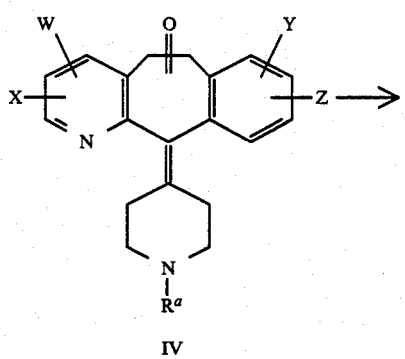

IV

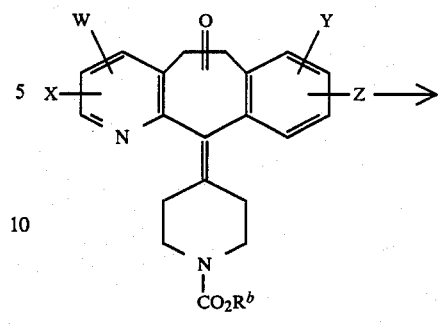

X

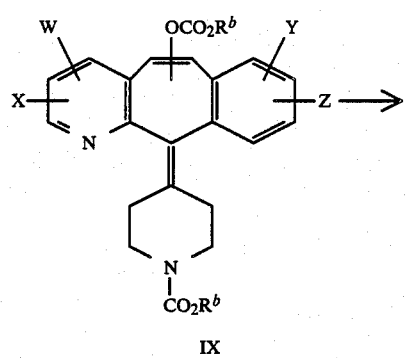

IX

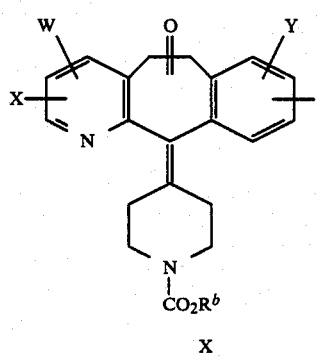

X

Compound IX may be prepared by reacting the bridgehead carbonyl compound of formula IV with an appropriate chloroformate, e.g., phenyl chloroformate, alkyl chloroformate, etc. to generate the enol carbonate on the bridgehead and the appropriate carbamate on the piperidylidene ring. For example, $R^b$ in phenylchloroformate is phenyl; $R^b$ in 2,2,2-trichloroethylchloroformate is 2,2,2-trichloroethyl, etc. Reactions may be run at temperatures ranging from about 70° C. to about 100° C., in an inert solvent, such as toluene. Furthermore, an organic base, such as triethylamine may be added.

The bridgehead carbonate moiety of Compound IX may be removed via mild aqueous base hydrolysis, for example with NaOH, K₂CO₃, etc., preferably at room temperature to yield compound X. The progress of the reaction may be monitored by thin layer chromatography to prevent removal of the carbamate group.

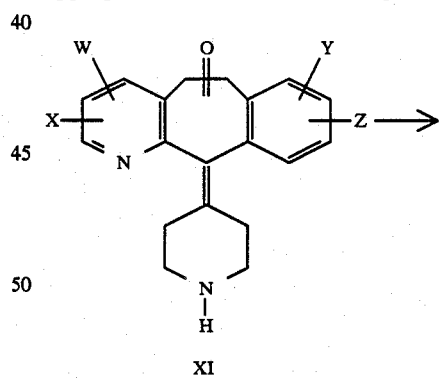

XI

Compound X may be treated with aqueous acid (e.g., HCl) or base (e.g., KOH) with heating, usually at about 100° C., to form the unsubstituted piperidylidene amine (R is hydrogen) Compound XI.

Alternatively, depending upon the nature of $R^b$, as determined by one of skill in the art, compound X may be treated with an organometallic reagent (e.g., CH₃Li), a reducing agent (e.g., Zn in acid), or hydrogen with an appropriate catalyst to form compound XI.

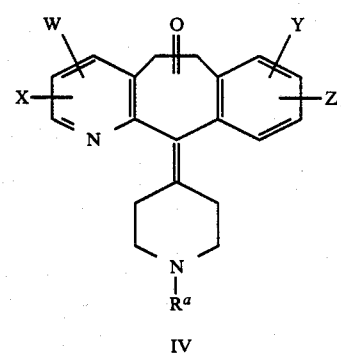

IV

Compound IV above may be formed by reacting compound XI with the appropriate alkyl halide (R^aX) in an inert solvent, such as THF, diethyl ether, toluene, DMF or acetonitrile in the presence of base, such as triethylamine.

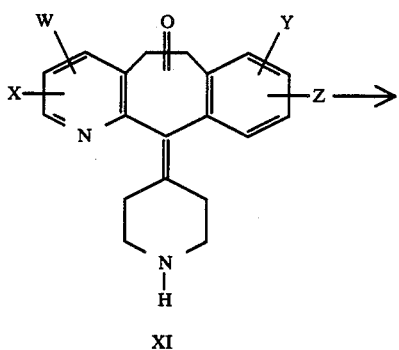

XI

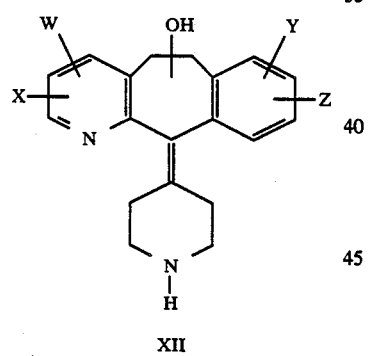

XII

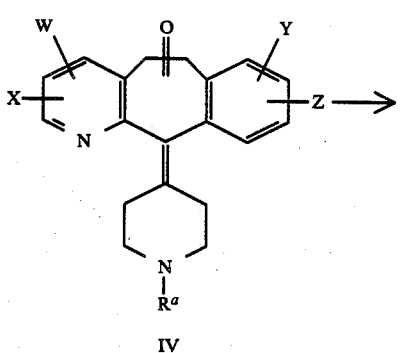

IV

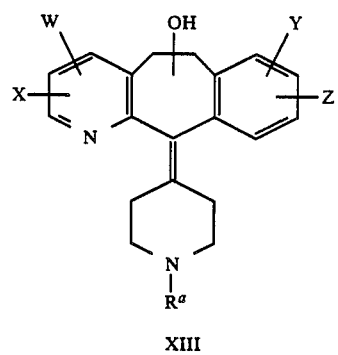

XIII

The bridgehead carbonyl of compound XI or IV may be reduced to an hydroxy group by treating compound XI or IV with an appropriate reducing agent, such as NaBH$_4$ in CH$_3$OH or LiAlH$_4$ in ether to produce a compound of formula XII or XIII respectively.

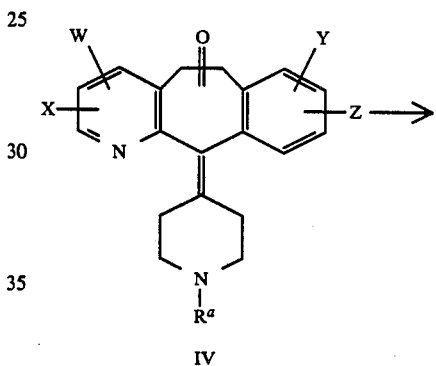

IV

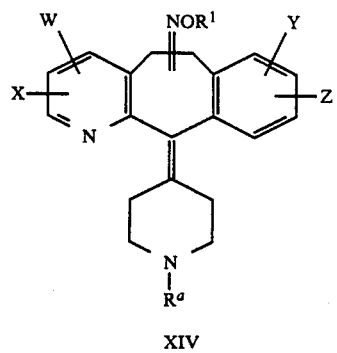

XIV

A compound of formula IV may be treated with an appropriate amine in a protic solvent under anhydrous conditions to produce a compound of formula XIV. A representative example of an amine useful herein is hydroxylamine, which reacts with compound IV at room temperature.

Alternatively, the unsaturated ketone compound VIa which is a chloro substituted compound of VI may be produced via cyclization of the unsaturated nitrile compound VIIa with polyphosphoric acid in the reaction scheme set forth below:

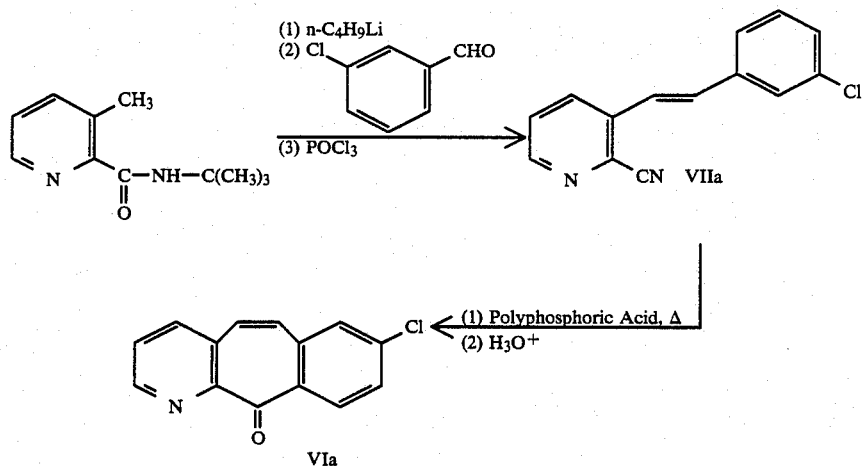
Although the unsaturated nitrile VIIa may be predominantly the trans isomer, the strongly acidic conditions of the cyclization will isomerize the trans to the cis isomer which can then close to the unsaturated aza ketone VIa.
The 6-hydroxy substituted compounds of the invention may also be prepared by the following reaction scheme using known techniques:
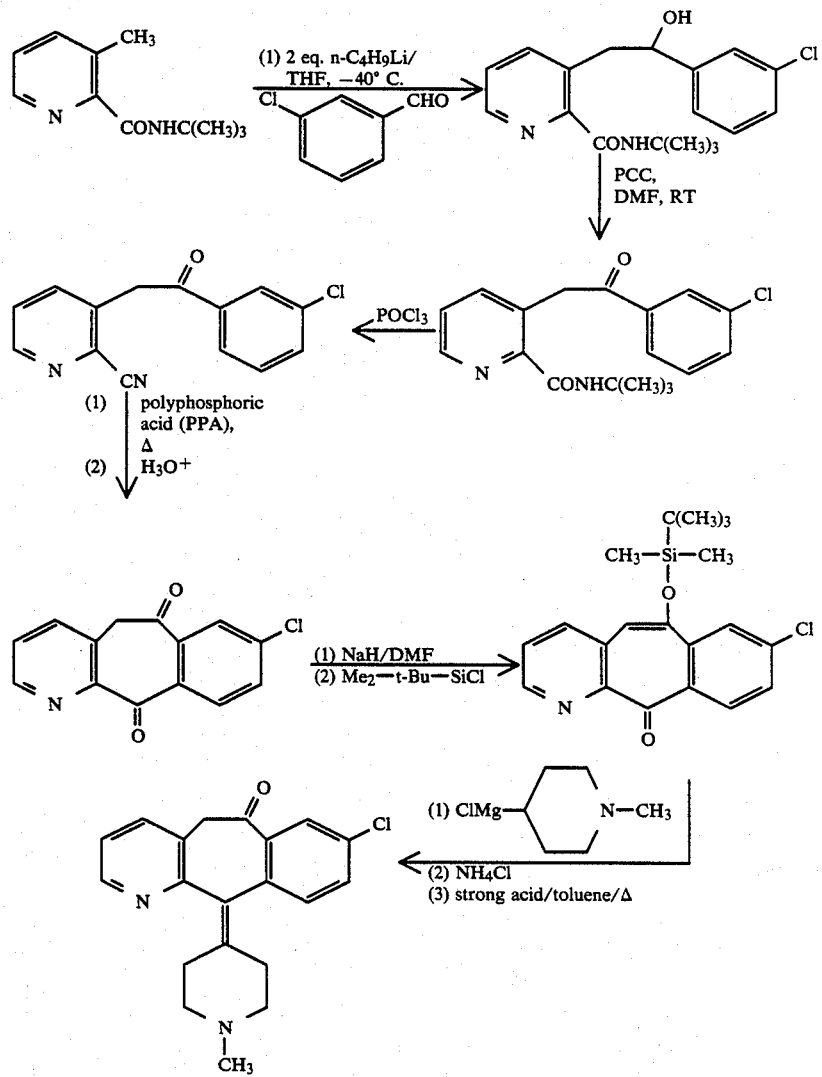

-continued
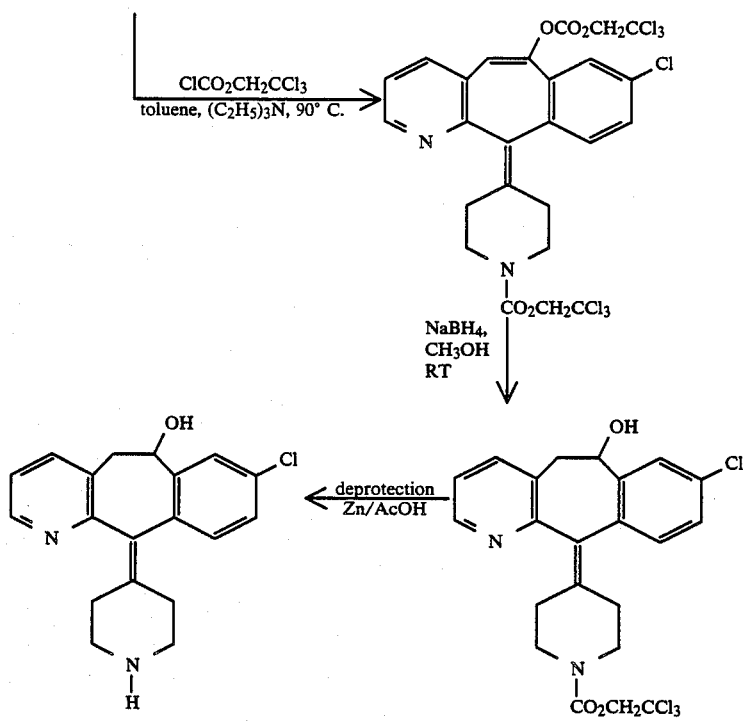
The strong acid in the above scheme can be, for example, sulfuric acid at about 60° C. The deprotection step may be accomplished, for example, by use of Zn and CH₃COOH.
Likewise, the 5-hydroxy substituted compounds of the invention may be prepared using known techniques by the following reaction scheme:
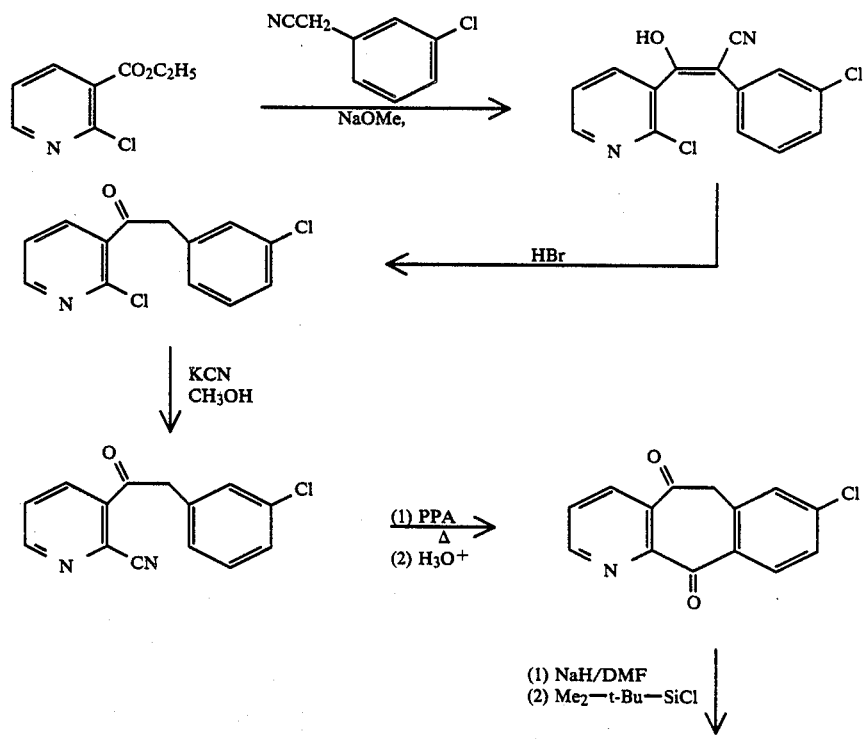

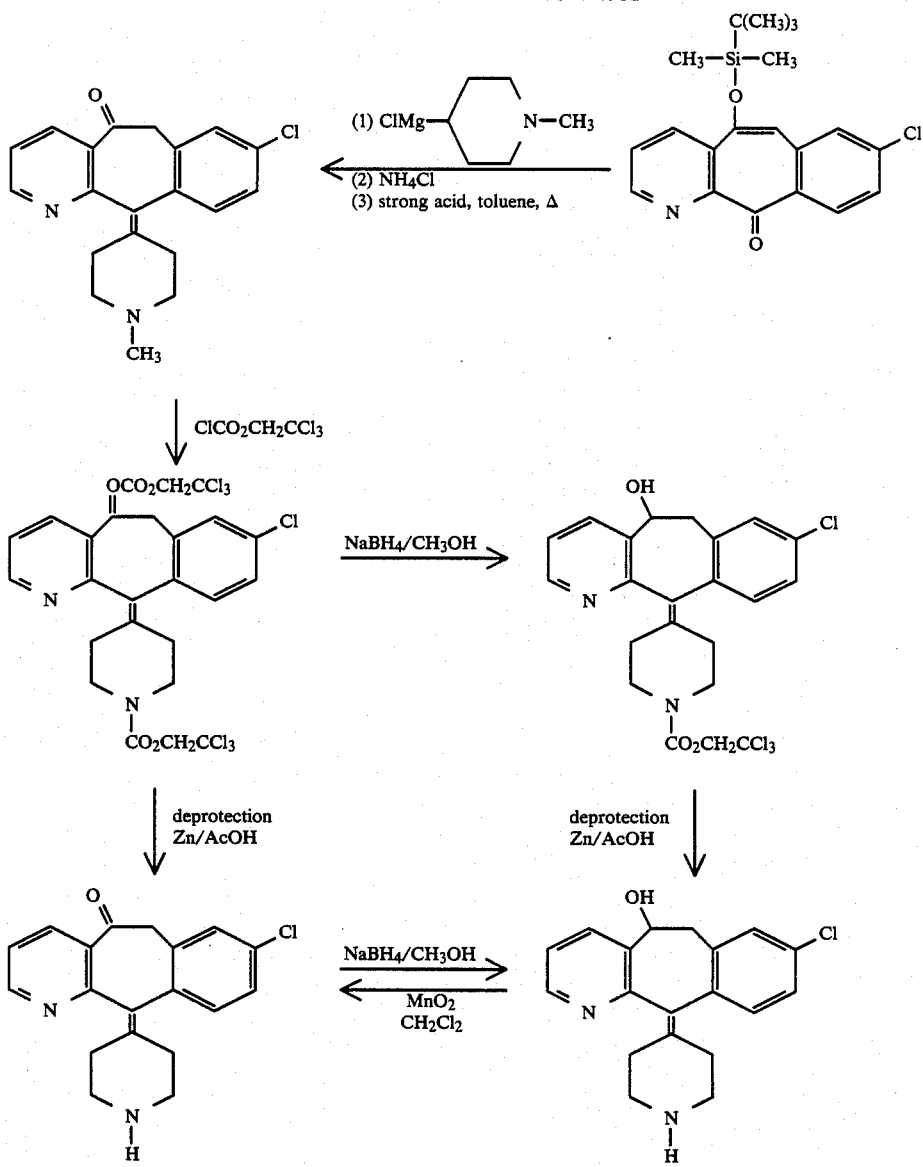
The 5- and 6-keto substituted compounds of the invention can be prepared from the corresponding 5- or 6-hydroxy substituted compounds by, for example, oxidation with $MnO_2$ in $CH_2Cl_2$.
The 3-hydroxy substituted compounds of the invention may be prepared by the reaction scheme described below:
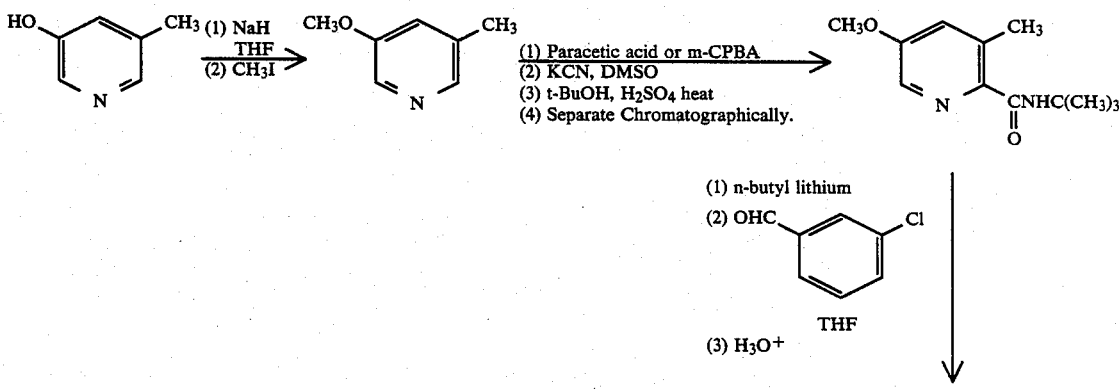

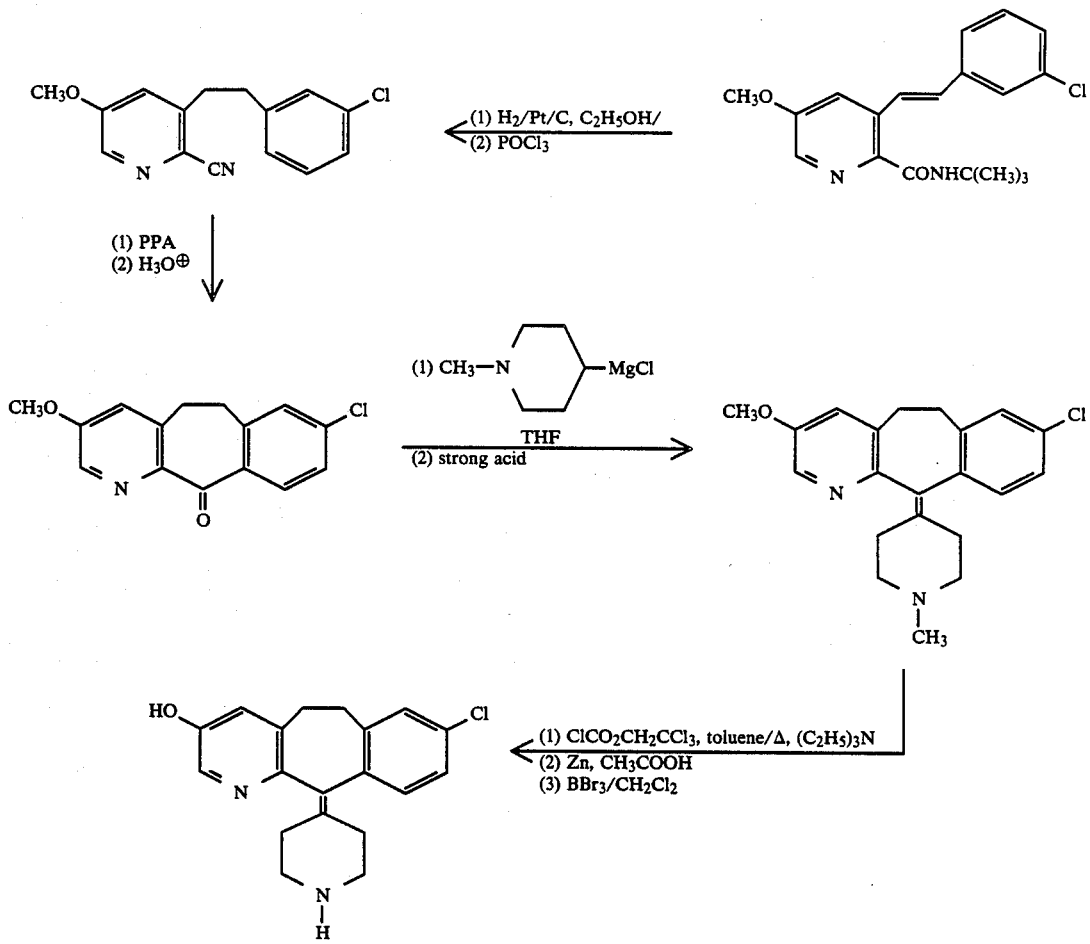

The compounds of the invention may alternatively be prepared and isolated from human and monkey urine after oral dosing with 8-chloro-6,11-dihydro-11-(1-ethoxycarbonyl-4-piperidylidene)-5H-benzo[5,6]cyclohepta[1,2-b]pyridine. Extraction of the urine samples with CH₂Cl₂ and purification by HPLC using reverse phase columns provided a mixture containing about 50% by weight of the compound 8-chloro-6,11-dihydro-11-(4-piperidylidene)-5H-benzo[5,6]cyclohepta[1,2-b]pyridin-5-ol and about 32% by weight of the compound 8-chloro-6,11-dihydro-11-(4-piperidylidene)-5H-benzo[5,6]-cyclohepta[1,2-b]pyridin-6-ol and also separately the compound 8-chloro-6,11-dihydro-11-(4-piperidylidene)-5H-benzo[5,6]cyclohepta[1,2-b]pyridin-3-ol. The yield of the metabolites may be increased by treatment of the urine with glucuronidase prior to extraction with CH₂Cl₂.

In the above processes it is sometimes desirable and/or necessary to protect certain A, B, W, X, Y, Z or R groups during the reactions. Conventional protecting groups are operable. For example, the groups listed in column 1 of the following table may be protected as indicated in column 2 of the table:

| 1. Group to be Protected | 2. Protected Group |
|---|---|
| —COOH | —COOalkyl, —COObenzyl, —COOphenyl |
| $\diagdown$NH$\diagup$ | N—CO₂alkyl, N—CO₂benzyl, N—CO₂CH₂CCl₃ |
| $\diagdown$C=O$\diagup$ | (cyclic ketals) |
| —OH | (tetrahydropyranyl ether) |
| —NH₂ | (succinimide) |

Of course, other protecting groups well known in the art may be used. After the reaction or reactions, the protecting groups may be removed by standard procedures.

The compounds of the invention possess antihistaminic properties which may be assessed by test procedure A below. Test procedure A, "Prevention of histaminic-induced lethality" demonstrates basic antihistaminic activity of representative compounds of structural formula I. Greater protection against histamine lethality is indicative of strong antihistaminic properties.

Test procedures B, C and D demonstrate the extent of CNS activity induced by the compounds of the invention. The presence of strong CNS activity indicates a high probability of sedation caused by the compounds, a typically undesirable side effect of antihistamines. Consequently, a low level of CNS activity is preferred in most circumstances.

Antihistamine Activity Assay

A. Prevention of histamine-induced lethality in guinea pigs

The compounds shown below in Table A were evaluated for antihistamine activity by their ability to protect female albino guinea pigs (250-350 g) against death induced by the intravenous injection of histamine dihydrochloride at 1.1 mg/kg, which is approximately twice the $LD_{99}$. Doses of the antagonists were administered orally to separate groups of fasted animals 1 hour prior to the challenge with histamine and protection from death recorded for 30 minutes after histamine. $ED_{50}$ values were determined for each drug by probit analysis.

CNS Activity Assays

B. Antagonism of Physostigmine Lethality

The physostigmine-induced lethality test is indicative of CNS activity and the test described is a modification of the technique reported by COLLIER et al., *Br. J. Pharmac.*, 32, 295-310 (1968). Physostigmine salicylate (1.0 mg/kg s.c.) produces 100% lethality when administered to mice grouped 10 per plastic cage (11×26×13 cm). Test agents were administered orally 30 minutes prior to physostigmine. The number of survivors were counted 20 minutes after physostigmine administration.

C. Antagonism of Acetic Acid Writhing

The acetic acid writhing test is a second test useful for determining CNS activity, and is essentially that described by HENDERSHOT and FORSAITH, *J. Pharmac. Exp. Ther.*, 125, 237-240 (1959), except that acetic acid rather than phenylquinone was used to elicit writhing. Mice were injected with 0.6% aqueous acetic acid at 10 mg/kg i.p. 15 minutes after oral administration of the test drug. The number of writhes for each animal was counted during a 10 minute period starting 3 minutes after acetic acid treatment. A writhe was defined as a sequence of arching of the back, pelvic rotation and hind limb extension.

D. Antagonism of Electro-Convulsive Shock (ECS)

The ECS test is a third test useful for determining CNS activity. For the ECS test, a modification of the method of TOMAN et al., *J. Neurophysiol.*, 9, 231-239 (1946), was used. One hour after oral administration of the test drug or vehicle, mice were administered a 13 mA, 60 cycle a.c. electroconvulsant shock (ECS) for 0.2 seconds via corneal electrodes. This shock intensity produces tonic convulsions, defined as extension of the hind limbs, in at least 95% of vehicle-treated mice.

Of the above test procedures for measuring CNS activity, the physostigmine-induced lethality test is believed to be a major index of non-sedating characteristics, since it reflects mainly central anticholinergic potency which is believed to contribute to sedative activity.

Representative results of test procedure A with compounds of the invention are presented below in Table A.

TABLE A

Compound

| A | B | Y | Z | R | Dose mg/kg | % Survival |
|---|---|---|---|---|---|---|
| H, H | =O | —Cl | —H | —H | 1 PO | 40% |
| =O | H, H | —Cl | —H | —H | 1 PO | 100% |
| H, OH | H, H | —Cl | —H | —H | 5 PO | 80% |
| H, H | H, OH | —Cl | —H | —CH$_3$ | 1 PO | 80% |
| H, H | =NOH | —Cl | —H | —CH$_3$ | 1 PO | 100% |
| H, H | H, OC(O)CH$_3$ | —Cl | —H | —CH$_3$ | 1 PO | 100% |

(Antihistamine Activity)

As seen from the data of Table A, the compounds of structural formula I exhibit antihistaminic properties to varying degrees. Consequently, it is within the scope of this invention to use each of these compounds when clinically appropriate. For example, if strong antihistaminic activity is necessary, such a compound could be chosen by the clinician. Alternatively, if weak antihistaminic activity is required, a different compound of the invention would be utilized by the clinician.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets may be comprised of from about 5 to about 70 percent active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in polyethylene glycol and/or polypropylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxy-methylcellulose and other well-known suspending agents.

Liquid form preparations may also include solutions for intranasal administration.

Aerosol preparations suitable for inhalation may include solutions and solids in powder form, which may be in combination with a pharmaceutically acceptable carrier, such as an inert compressed gas. Inhalation aerosols may be packaged in a pressure resistant container, which may have a metered dose feature suitable for administration into the oral cavity for inhalation, or into the nasal passageways, thereby delivering a precise amount of aerosol per use.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form prepara-tion may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions, aerosols and/or emulsions and can be included in a transdermal patch of the matrix of reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form. The compositions can, if desired, also contain other therapeutic agents.

The quantity of active compound in a unit dose of preparation may be varied or adjusted from about 0.1 mg to 1000 mg, more preferably from about 1 mg. to 100 mg, according to the particular application. The appropriate dosage can be determined by comparing the activity of the compound with the activity of a known antihistaminic compound such as 8-chloro-6,11-dihydro-11-(1-ethoxycarbonyl-4-piperidylidene)-5H-benzo[5,6]cyclohepta[1,2-b]pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgement of the attending clinician considering such factors as age, condition and size of the patient as well as severity of the symptom being treated. A typical recommended dosage regimen is oral administration of from 0.25 to 100 mg/day, preferably 10 to 20 mg/day, in two to four divided doses to achieve relief of the symptoms.

The following examples are intended to illustrate, but not to limit, the present invention.

PREPARATIVE EXAMPLE 1

8-Chloro-11H-benzo[5,6]cyclohepta[1,2-b]pyridin-11-one

Reflux a mixture of 8-chloro-5,6-dihydro-1H-benzo[5,6]cyclohepta[1,2-b]pyridin-11-one (25.99 g, 0.107 mol.), recrystallized N-bromosuccinimide (21.35 g, 0.120 mol) and 167 mg (0.102 mmol) of azobisisobutyrylnitrile in 400 mL of carbontetrachloride under an argon atmosphere for 1.25 hours. Cool the solution slowly to 50° C. and filter off the resultant precipitate.

Reflux the precipitate with 1,8-diazabicyclo[5.4.0]undec-7-ene ("DBU") (20 mL, 0.134 mol) in $CH_2Cl_2$ (400 mL) for 1 hour. Wash with water (3X), dry over magnesium sulfate, filter and concentrate in vacuo. Recrystallize the crude product from $CH_2Cl_2$/toluene to give the title compound as colorless needles (8.93 g, yield 35%).

ALTERNATIVE PREPARATIVE EXAMPLE 1

8-Chloro-11-benzo[5,6]cyclohepta[1,2-b]pyridin-11-one

Reflux a mixture of 10.23 gm (44.5 mmol) of 8-chloro-5,6-dihydro-11H-benzo[5,6]cyclohepta[1,2-b]pyridine-11-one and 20.96 gm (92.3 mmol) of 2,3-dichloro-5,6-dicyano-1,4-benzoquinone(DDQ) in 100 mL of dioxane under an atmosphere of nitrogen for 5 days. Add additional amounts (10.06 gm and 8.02 gm) of DDQ after 3 and 4 days, respectively. Cool the mixture to room temperature and pour into 200 mL of ether. Extract the mixture two times with 5% aqueous HCl. Combine the aqueous portions and wash three times with ether, each time filtering mixture. Basify the mixture with solid sodium hydroxide and filter off and dry the precipitate. Recrystallize the solid from hot toluene/hexane to provide the title compound (3.62 g–36% yield).

PREPARATIVE EXAMPLE 2

A. 5-Methoxy-8-chloro-11H-benzo[5,6]cyclohepta[1,2-b]pyridin-11-one

B. 6-Methoxy-8-chloro-11H-benzo[5,6]cyclohepta[1,2-b]pyridin-11-one

Add $Br_2$ (5.10 mL, 99 mmol) to a mixture of the title compound of Preparative Example 1 (8.15 g, 33.7 mmol) and powdered $AgNO_3$ (23.19 g, 137 mmol) in 300 mL of dry methanol at room temperature under an argon atmosphere. After 8 hours, add additional $AgNO_3$ (5.90 g, 34.7 mmol) followed by additional $Br_2$ (1.7 mL, 33.0 mmol). After 0.5 hours pour the mixture into water and extract (4X) with $CH_2Cl_2$. Combine the organic phases, dry over magnesium sulfate, filter and concentrate in vacuo to give a mixture of the crude bromo ethers, title compounds A and B above.

Dissolve the crude product in $CH_2Cl_2$ (200 mL) at room temperature and place under an argon atmosphere. Add DBU (20 mL, 134 mmol) and reflux for 1.3 hours. Add additional DBU (10 mL, 67 mmol) and reflux the mixture for an additional hour. Pour the mixture into water and extract (3X) with $CH_2Cl_2$. Combine the organic phases, wash with water and dry over magnesium sulfate. Filter and concentrate in vacuo. The two isomeric vinyl ethers title compounds A and B are separated and purified via flash chromatography [40%–75% ethyl acetate in hexanes] and recrystallize from ethyl acetate hexanes to give title compound A (1.51 g, 14.3%, mp 156° to 158° C.) and title compound B (3.68 g, 35%, mp 161° to 162° C.).

PREPARATIVE EXAMPLE 3A

6-Methoxy-8-chloro-11-(1-methyl-4-piperidinyl)benzo[5,6]cyclohepta[1,2-b]pyridin-11-ol Add a 1.5M Grignard solution of N-methyl 4-chloropiperidine in tetrahydrofuran (THF) dropwise over a 10 minute period (17.2 mL, 26.6 mmol) to the title compound of Preparative Example 2A (6.0 g, 22.1 mmol) in THF (80 mL) at 0° C. under an Argon atmosphere. Quench the reaction after 1 hour with water and extract (3X) with ethyl acetate. Combine the organic portions, wash with brine, dry over sodium sulfate, filter and concentrate in vacuo. Chromatograph on silica gel (5% $CH_3OH$ in $CH_2Cl_2$) to give the title compound (5.01 g, 61%) which may be recrystallized from isopropyl ether to give a solid in the form of white needles (mp 159°–160° C.).

PREPARATIVE EXAMPLE 3B

5-Methoxy-8-chloro-11-(1-methyl-4-piperidinyl)benzo[5,6]cyclohepta[1,2-b]pyridin-11-ol Add a 1.5M Grignard solution of N-methyl 4-chloropiperidine (150 mL, 22.5 mmol) in THF dropwise over a 7 minute period to title compound B of Preparative Example 2 (5.00 g, 18.4 mmol) in THF (70 mL) at 0° C. under an argon atmosphere. Quench the reaction after 30 minutes with a saturated solution of $NH_4Cl$ (pH 8) and extract (3X) with $CHCl_3$. Combine the organic portions, wash with brine, dry over sodium sulfate, filter and concentrate in vacuo. Purify with flash chromatography ($CH_3OH$ 5% in $CH_2Cl_2$) to give the title compound (3.60 g, 53%) as a solid. The solid may be recrystallized from isopropyl ether to give a white powder (mp 168°–170° C.).

PREPARATIVE EXAMPLE 4A

8-Chloro-11-(1-methyl-4-piperidylidene)-5,11-dihydro-6H-benzo[5,6]cyclohepta[1,2-b]pyridin-6-one Mix the title compound of Preparative Example 3A (2.00 g, 5.39 mmol) slowly in 95% aqueous $H_2SO_4$ (30 ml). Stir at room temperature under an argon atmosphere for 30 minutes and add trifluoromethyl sulfonic acid (30 mL). Heat the mixture to 115° C. and maintain for one hour. Cool the mixture to room temperature, pour onto ice, basify with 25% aqueous NaOH and extract (2X) with $CH_2Cl_2$. Combine the organic portions and wash with brine. Dry over sodium sulfate, filter, and concentrate in vacuo to give the title compound (1.41 g, 77%). Recrystallize the material from ethyl acetate/isopropyl ether to give the title compound as a granular solid (1.12 g, 61%, mp 181°–183° C.).

PREPARATIVE EXAMPLE 4B

8-Chloro-11-(1-methyl-4-piperidylidene)-6,11-dihydro-5H-benzo[5,6]cyclohepta[1,2-b]pyridin-5-one Dissolve the title compound of Preparative Example 3B (4.26 g) in $CH_3OH$ (6 mL) at 0° C. under an argon atmosphere. Add slowly a cooled solution of 92% aqueous $H_2SO_4$ (54 mL). Allow the mixture to warm to room temperature for 35 minutes. Pour the solution onto ice, basify with aqueous NaOH (25%), and extract with methylene chloride (3X). Combine the organic portions, wash with brine and dry over sodium sulfate. Filter and concentrate in vacuo. Triturate the residue with isopropyl ether to give an intermediate, 8-chloro-11-hydroxy-11-(1-methyl-4-piperidinyl)-6,11-dihydro-5H-benzo[5,6]cyclohepta[1,2-b]pyridin-5-one as a white solid (3.58 g., 92%, m.p. 170° to 174° C. as HCl salt).

Dissolve the intermediate compound (3.58 g, 10.0 mmol) in trifluoromethane sulfonic acid (50 mL) and heat to 45° C. under an argon atmosphere for 3 hours. Pour the mixture onto ice, basify with aqueous NaOH (25% w/v), and extract with $CHCl_3$ (3X). Combine the organic portions, wash with brine and dry over sodium sulfate. Filter and concentrate in vacuo. Chromatograph on silica gel (5% $CH_3OH$ in $CH_2Cl_2$) to give the title compound as an off white solid (1.703 g, 50%, 58% based on recovered starting material). An analytical sample was prepared by recrystallization of the product with ethyl acetate/isopropyl ether (mp 162°–163° C.).

PREPARATIVE EXAMPLE 5

Ethyl 4-(8-chloro-6-ethoxycarbonyloxy-5,6-dihydro-11H-benzo[5,6]cyclohepta[1,2-b]pyridin-11-ylidene)-1-piperidine carboxylate Add dropwise a mixture of ethyl chloroformate (1.34 mL, 14.0 mmol) in toluene (12 mL) to a solution of the title compound of Preparative Example 4A (952 mg, 2.81 mmol) and in triethylamine (590 mL, 4.23 mmol) at 80° C. under an argon atomsphere. After 30 minutes cool the mixture to room temperature, filter and concentrate in vacuo. Purify the crude product via flash chromatography [5% $CH_3OH$ in $CH_2Cl_2$] to yield the title compound as a glass (1.11 g., 84%).

PREPARATIVE EXAMPLE 6

Ethyl 4-(8-chloro-5-ethoxycarbonyloxy-5,6-dihydro-11H-benzo[5,6]cyclohepta[1,2-b]pyridin-11-ylidene)-1-piperidine carboxylate Dissolve the title compound of Preparative Example 4B (617 mg, 1.82 mmol) and triethylamine (0.50 mL, 3.58 mmol) in toluene (12 mL) at 80° C. under an argon atmosphere. Add dropwise over 2 minutes ethyl chloroformate (0.87 mL, 9.10 mmol). After 25 minutes cool the mixture to room temperature, filter, and concentrate in vacuo. Purify the crude product via flash chromatography (1% $CH_3OH$ in $CH_2Cl_2$) to yield the title compound as a glass (834 mg, 98%).

EXAMPLE 1

8-Chloro-11-(4-piperidylidene)-5,11-dihydro-6H-benzo[5,6]cyclohepta[1,2-b]pyridin-6-one Mix the title compound of Preparative Example 5 (1.40 g., 2.99 mmol) and aqueous KOH (20 mL, 13% w/v) in ethanol (15 mL) and reflux under an argon atmosphere for 42 hours. Pour the mixture into water and extract (4X) with $CH_2Cl_2$. Combine the organic portions, wash with brine, dry over sodium sulfate, filter and concentrate in vacuo. Purify the residue via flash chromatography (10–20% $CH_3OH$ in $CH_2Cl_2$) and recrystallize from $CH_2Cl_2$/pentane to give the title compound as a yellowish solid (6.55 mg, 67% mp 207°–209° C. (dec)).

EXAMPLE 2

6-Hydroxy-8-chloro-11-(4-piperidylidene)-6,11-dihydro-5H-benzo[5,6]cyclohepta[1,2-b]pyridine Mix the title compound of Example 1, (0.29 g, 0.893 mmol) in $CH_3OH$ (14 mL) at 0° C. under an argon atmosphere. Add $NaBH_4$ (165 mg, 4.36 mmol) in 3 portions. After 30 minutes, pour the mixture into water and extract (3X) with $CH_2Cl_2$. Combine the organic portions, wash once with brine, dry over sodium sulfate, filter and concentrate in vacuo to give a crude product. Purifiy via flash chromatography [5–10% $CH_3OH$ saturated with $NH_3$ in $CH_2Cl_2$] to give the title compound, which can be triturated with isopropyl ether/pentane to give an off-white solid (249 mg, 85%).

EXAMPLE 3

8-Chloro-6-hydroxyimino-11-[1-methyl-4-piperidylidene]-6H-benzo[5,6]cyclohepta[1,2-b]pyridine Add the title compound of Preparative Example 4A (369 mg, 1.1 mmol) to a solution of $NH_2OH·HCl$ (190 mg, 2.7 mmol), dry pyridine (0.245 mL, 3.0 mmol), water (1.0 mL) and absolute ethanol (20 mL). Stir the reaction for 17 hours at room temperature, and quench with water. Basify the reaction to pH 10 with dilute NaOH. Extract the solution with $CH_2Cl_2$ (3X), combine the organic phases and dry over sodium sulfate. Filter the organic phase and concentrate to a yellowish oil. Triturate the oil with pentane and isopropyl ether to yield the title compound as a white powder (387 mg, 98%, m.p. 172°–175° C.).

EXAMPLE 4

8-Chloro-11-(1-methyl-4-piperidylidene)-5,11-dihydro-6H-benzo[5,6]cyclohepta[1,2-b]pyridin-6-ol Add $NaBH_4$ (155.7 mg, 4.1 mmol) to an ice-bath cooled solution of the title compound of Preparative Example 4A (277 mg, 0.87 mmol) in $CH_3OH$ (14 mL) under an argon atmosphere. Stir the reaction while warming to room temperature (1 hour). Extract with $CH_2Cl_2$ (2×150 mL) and wash with brine. Dry the organic phase over sodium sulfate, filter and concentrate in vacuo to give a yellowish foam-solid. Recrystallize from ethyl acetate and diethyl ether to give the title compound (270 mg, 97%, mp 222°–225° C.).

EXAMPLE 5

8-Chloro-11-(1-methyl-4-piperidylidene)-5,11-dihydro-6H-benzo[5,6]cyclohepta[1,2-b]pyridin-6-ol Dissolve the title compound of Example 4 (286 mg, 0.84 mmol) in $CH_2Cl_2$ (8.5 mL) and add pyridine (1.26 mL, 15.6 mmol) under an argon atmosphere. Add acetic anhydride (0.84 mL, 8.9 mmol), and warm to 35° C. (oil bath temperature) for 6 hours. Cool to room temperature and quench with water. Extract the product with $CH_2Cl_2$ (2×150 mL) and wash with brine. Dry the organic phase over sodium sulfate, filter and concentrate in vacuo. Azeotrope with toluene to give the title compound, a white solid, as the hydrochloride hemihydrate (350 mg, 97%). An analytical sample was prepared by recrystallization from ethylacetate (mp 252–254° C. (dec)).

EXAMPLE 6

8-Chloro-11-(4-piperidylidene)-6,11-dihydro-5H-benzo[5,6]cyclohepta[1,2-b]pyridin-5-one Mix the title compound of Preparative Example 6 (897 mg, 1.91 mmol) and aqueous KOH (20 mL, 13% w/v) in ethanol (15 mL) and reflux under an argon atmosphere for 25 hours. Pour the mixture into water and extract with $CHCl_3$ (3X). Combine the organic portions, wash with brine, dry over sodium sulfate, filter, and concentrate in vacuo. Purify the residue via flash chromatography (2% $CH_3OH$ saturated with $NH_3$ in $CH_2Cl_2$) and triturate with isopropyl ether to give the title compound as a white solid (417 mg, 67%, mp 194°–196° C. (dec)).

EXAMPLE 7

5-Hydroxy-8-chloro-11-(4-piperidylidene)-6,11-dihydro-5H-benzo[5,6]cyclohepta[1,2-b]pyridine Mix the title compound of Example 6 (400 mg, 1.23 mmol) in CH₃OH (20 mL) at 0° C. under an argon atmosphere, and add in 3 portions NaBH₄ (total 231 mg, 6.10 mmol). After 30 minutes, pour the mixture into water and extract (3X) with ethyl acetate. Combine the organic portions, wash with brine, dry over sodium sulfate, filter and concentrate in vacuo. Triturate the solid with isopropyl ether/ethyl acetate to give the title compound as a white solid (351 mg, 87%).

The following formulations exemplify some of the dosage forms of the compositions of this invention. In each, the term "active compound" designates for purposes of the formulation the compound, 8-chloro-6,11-dihydro-11-(4-piperidylidene)-5H-benzo[5,6]cyclohepta[1,2-b]pyridine-5-ol, or a pharmaceutically acceptable salt or solvate thereof. However, any other compound falling within the scope of formula I can be used.

Pharmaceutical Dosage Form Examples
Example A
Tablets

| No. | Ingredient | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

Example B
Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C
Parenteral

| Ingredient | mg/vial | mg/vial |
|---|---|---|
| Active Compound Sterile Powder | 100 | 500 |

Add sterile water for injection or bacteriostatic water for injection, for reconstitution.

Example D
Injectable

| Ingredient | mg/vial | mg/vial |
|---|---|---|
| Active Compound | 100 | 500 |
| Methyl p-hydroxybenzoate | 1.8 | 1.8 |
| Propyl p-hydroxybenzoate | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65–70° C.
2. Cool to 25–35° C. Charge and dissolve the sodium bisulfite, disodium edetate and sodium sulfate.
3. Charge and dissolve drug.
4. Bring the solution to final volume by added water for injection.
5. Filter the solution through 0.22 membrane and fill into appropriate containers.
6. Terminally sterilize the units by autoclaving.

Example E
Nasal Spray

| | mg/ml |
|---|---|
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |
| Sodium Hydroxide 1 N Solution to adjust pH | — |
| Water Purified USP to make | 1.0 ml |

Example F
Ointment

| Formula | mg/g |
|---|---|
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a portion of the mineral oil. Mix and heat to 65° C., a weighed quantity of white petroleum, the remaining mineral oil and benzyl alcohol, and cool to 50°–55° C. with stirring. Add the dispersed active compound to the above mixture with stirring. Cool to room temperature.

Example G
Cream

| Formula | mg/g |
|---|---|
| Active Compound | 1.0–20.0 |
| Stearic Acid, USP | 60.0 |
| Glyceryl Monostearate | 100.0 |

-continued

Example G
Cream

| Formula | mg/g |
|---|---|
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37°-40° C. Mix uniformly with stirring and cool to room temperature.

The relevant teachings of all published references cited herein are incorporated by reference.

While the present invention has been described in connection with the certain specific embodiments thereof, it will be evident to one of ordinary skill in the art that many alternatives, modifications and variations may be made. All such alternatives, modifications and variations are intended to be included within the spirit and scope of the invention.

We claim:

1. A compound represented by structural formula I:

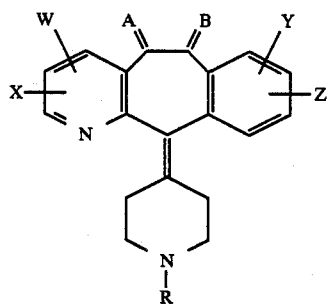

or a pharmaceutically acceptable salt or solvate thereof, wherein:
R represents H or alkyl having 1 to 20 carbon atoms; one of A and B represents H and OC(O)R$^1$, =NOR$^1$ or O—(CH$_2$)$_n$—O—, and the other represents H$_2$ or one of the above listed groups;
W, X, Y and Z may be the same or different and each independently represents H, halo, alkyl having 1 to 20 carbon atoms, —CF$_3$, —NO$_2$, —OC(O)R$^1$, —SR$^1$, —OR$^1$, —CO$_2$—R$^1$ or —N(R$^1$)$_2$;
R$^1$ is H, alkyl having 1 to 20 carbon atoms, or aryl having 6 to 15 carbon atoms, and in —N(R$^1$)$_2$, R$^1$ can be alkanediyl having 1 to 20 carbon atoms; and n is 2, 3 or 4 with the proviso that when A is =NOR$^1$, R$^1$ is other than H.

2. A compound as defined in claim 1 wherein R represents alkyl having 1 to 20 carbon atoms.

3. A compound as defined in claim 1 where R represents H.

4. A compound as defined in claim 2 where R represents lower alkyl having 1 to 6 carbon atoms.

5. A compound represented by the structural formula I:

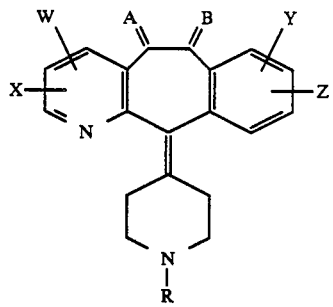

or a pharmaceutically acceptable salt or solvate thereof, wherein:
R represents H or alkyl having from 1 to 20 carbon atoms, such that
(1) when R represents alkyl having 1 to 20 carbon atoms, at least one of A and B represents a substituent group selected from H and OR$^1$, H and OC-(O)R$^1$, =NOR$^1$ or —O—(CH$_2$)$_n$—O—, and the other may represent H$_2$ or one of the above listed substituent groups;
W represents halo, alkyl having 1 to 20 carbon atoms, —CF$_3$, —NO$_2$, —OC(O)R$^1$, —SR$^1$, —OR$^1$, —CO$_2$R$^1$ or —N(R$^1$)$_2$;
X, Y and Z may be the same or different, and each independently represents H or one of the above defined W groups;
R$^1$ is H, alkyl having 1 to 20 carbon atoms or aryl having 6 to 15 carbon atoms, and in —N(R$^1$)$_2$, R$^1$ can be alkanediyl having from 1 to 20 carbon atoms;
n is 2, 3 or 4, and
(2) when R represents H,
A and B may be the same or different and each independently represents H$_2$, H and OR$^1$, H and OC-(O)R$^1$, =O, =NOR$^1$ or —O—(CH$_2$)$_n$—O—;
X, Y and Z may be the same or different and each independently represents H, halo, alkyl having 1 to 20 carbon atoms, —CF$_3$, —NO$_2$, —OC(O)R$^1$, —SR$^1$, —OR$^1$, —CO$_2$R$^1$ or —N(R$^1$)$_2$;
W represents halo, alkyl having 1 to 20 carbon atoms, —CF$^3$, —NO$_2$, —OC(O)R$^1$, —SR$^1$, —OR$^1$, —CO$_2$R$^1$ or —N(R$^1$)$_2$, with the provisos that when A and B both represent H$_2$, W is OR$^1$ and R$^1$ is H, and
R$^1$ and n are as defined above.

6. A compound as defined in claim 5 where R represents alkyl having 1 to 20 carbon atoms.

7. A compound as defined in claim 6 wherein R represents lower alkyl having 1 to 6 carbon atoms and A, B, W, X, Y and Z are as defined therein.

8. A compound as defined in claim 7 wherein R represents lower alkyl of from 1 to 3 carbon atoms and A, B, W, X, Y and Z are as defined therein.

9. A compound as defined in claim 5 wherein one of A and B is H$_2$ and the other of A and B represents H and OR$^1$, H and OC(O)R$^1$, =O, =NOR$^1$ or —O—(CH$_2$)$_n$O—, and W, X, Y, Z, R and R$^1$ are as defined therein.

10. A compound as defined in claim 5 wherein at least one of A and B represent H and OR$^1$ and W, X, Y, Z, R and R$^1$ are as previously defined.

11. A compound as defined in claim 5 wherein A and B represent $H_2$, W represents $OR^1$ and X, Y, Z, R and $R^1$ are as previously defined.

12. A compound as defined in claim 11 wherein $R^1$ represents H.

13. A compound as defined in claim 1 or 5 wherein at least one of Y and Z represents halo.

14. A compound as defined in claim 1 or 5 wherein one of Y and Z represents halo.

15. A compound of claim 14 wherein Y represents halo at position 8.

16. A compound as defined in claim 15 wherein Y represents chloro at position 8.

17. A compond as defined in claim 1 or 5 wherein W represents $OR^1$ at position 3.

18. A compound as defined in claim 17 wherein $R^1$ represents H.

19. A compound as defined in claim 5 where R represents H.

20. A compound having the name 3-hydroxy-8-chloro-11-[4-piperidylidene]-6,11-dihydro-5H-benzo[5,6]cyclohepta[1,2-b]pyridine, 8-chloro-11-(1-methyl-4-piperidylidene)-6,11-dihydro-5H-benzo[5,6]cyclohepta[1,2-b]pyridin-6-ol acetate or 8-chloro-6-hydroxyimino-11-[1-methyl-4-piperidylidene]-6H-benzo[5,6]cyclohepta[1,2-b]pyridine.

21. A pharmaceutical antiallergic composition comprising a compound as defined in claim 1 in an amount effective to treat allergy in combination with a pharmaceutically acceptable carrier.

22. A pharmaceutical antiallergic composition comprising a compound as defined in claim 5 in an amount effective to treat allergy in combination with a pharmaceutically acceptable carrier.

23. A method of treating allergy in a mammal comprising administering to said mammal an anti-allergic effective amount of a compound as defined in claim 1.

24. A method of treating allergy in a mammal comprising administering to said mammal an anti allergic effective amount of a compound as defined in claim 5.

* * * * *